United States Patent [19]
Allen et al.

[11] Patent Number: 5,320,633
[45] Date of Patent: Jun. 14, 1994

[54] METHOD AND SYSTEM FOR REPAIRING A TEAR IN THE MENISCUS

[75] Inventors: William C. Allen, Division of Orthopaedic Surgery, University of Missouri-Columbia, Health Sciences Center, Columbia, Mo. 65212; Michael G. Maurizi, Columbia, Mo.

[73] Assignee: William C. Allen, Columbia, Mo.

[21] Appl. No.: 988,454

[22] Filed: Dec. 10, 1992

[51] Int. Cl.$^5$ ............................................. A61B 17/04
[52] U.S. Cl. ..................................... 606/144; 128/898
[58] Field of Search ............... 606/139, 144, 148, 151, 606/213, 215, 220; 128/898; 623/11, 13; 24/706.3, 708.5, 709.5

[56] References Cited

U.S. PATENT DOCUMENTS

| | | | |
|---|---|---|---|
| 4,006,747 | 2/1977 | Kronenthal et al. | 606/144 |
| 4,586,502 | 5/1986 | Bedi et al. | 606/144 |
| 4,669,473 | 6/1987 | Richards et al. | 606/220 |
| 5,085,661 | 2/1992 | Moss | 606/139 |

Primary Examiner—Tamara L. Graysay
Attorney, Agent, or Firm—Senniger, Powers, Leavitt & Roedel

[57] ABSTRACT

A system for repairing a tear in the meniscus in the knee joint including a suture having a first leg, a second leg spaced from the first leg and a cross member connecting the first and second legs. An instrument for delivering the suture to the meniscus can be inserted through an incision in the knee and into the vicinity of the meniscus. A first end of the instrument enters the meniscus adjacent to a first side of the tear, passes through the meniscus and exits the meniscus on a second side of the tear in the meniscus generally opposite the first side of the tear. The instrument has a channel extending longitudinally of the instrument in which the first leg of the suture can be inserted. A push rod pushes the first leg and cross member generally lengthwise in the channel and into the meniscus where the suture closes the tear.

17 Claims, 3 Drawing Sheets

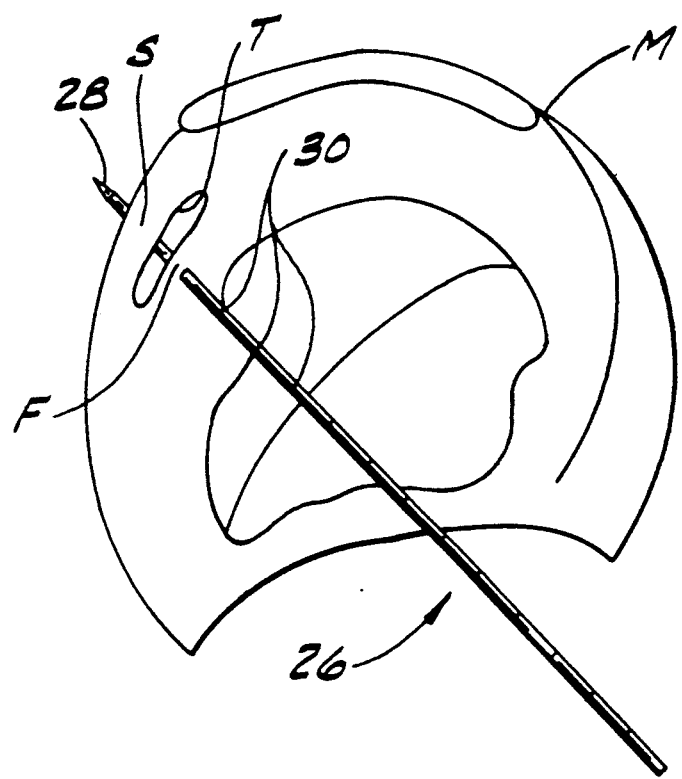

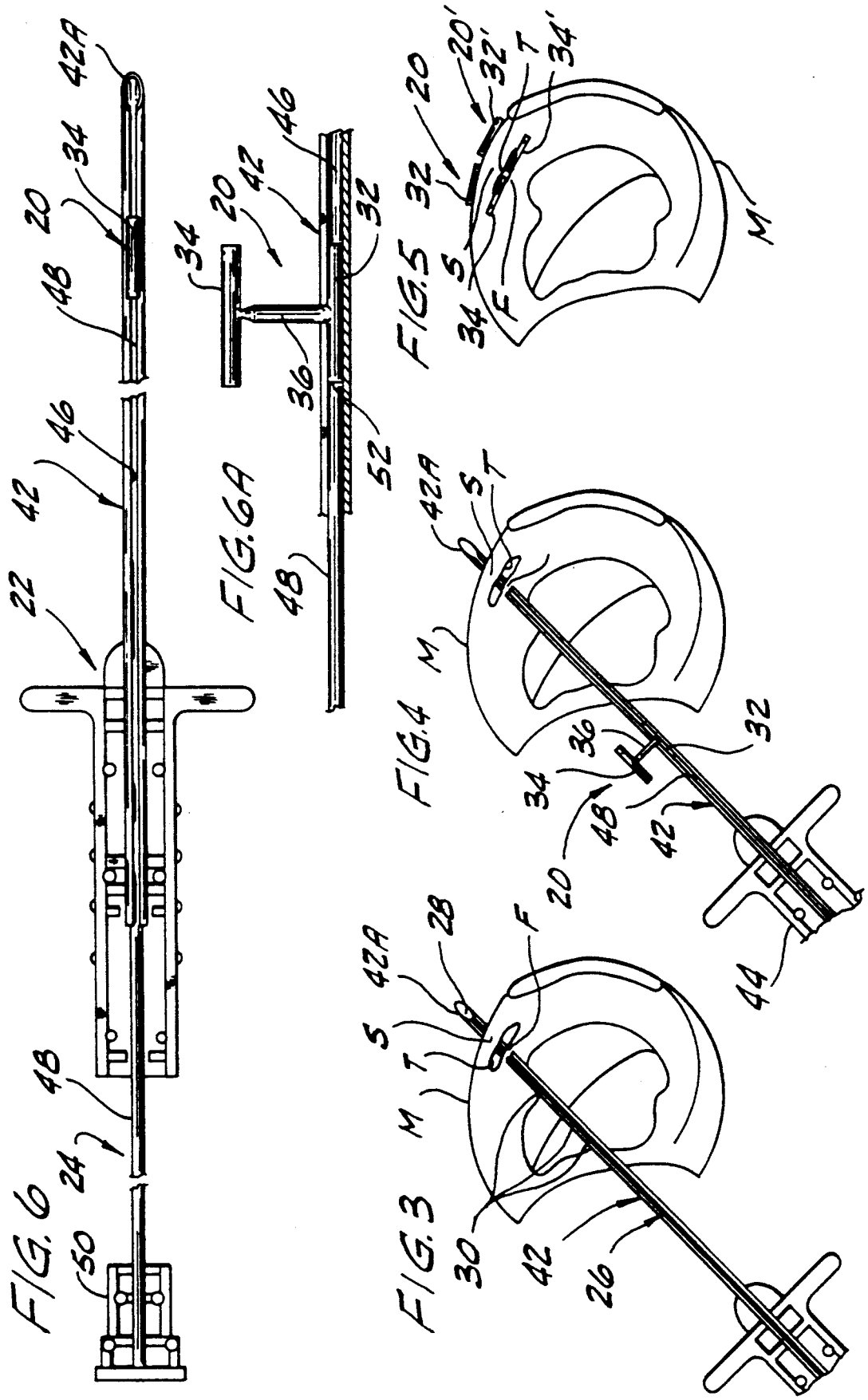

METHOD AND SYSTEM FOR REPAIRING A TEAR IN THE MENISCUS

SUMMARY OF THE INVENTION

This invention relates generally to methods and systems for repairing tears in cartilage and more particularly to a method and system for repairing a tear in the meniscus in the knee joint.

Injury to the knee involving a tear in the meniscus is a common occurrence, often in the context of athletic events, and is prevalent in the younger population. The meniscus is recognized as being vital to the biomechanical stability and protection of the knee joint. Damage to the meniscus can greatly increase the likelihood of the articular surfaces of the knee joint developing conditions such as osteoarthritis. Thus, in many instances it is desirable to repair the torn meniscus with the objective being to prevent instability of the knee joint and to prevent onset of conditions such as osteoarthritis.

Current methods for repairing tears in the meniscus are very technically challenging for the surgeon and present certain risks during the operation. These techniques require that a long needle with a suture be passed through the torn meniscus and the knee joint. The procedure, in which the needle must pass back and forth through the meniscus and knee joint, increases the risk of damage to the neurovascular structure about the knee. In addition, infectious or fistulous tracks may develop along the lines of suture placement into the knee joint. Many surgeons are dissuaded from attempting such this difficult procedure. In fact, the most common treatment for tears in the meniscus is to remove of some or all of the meniscus. This treatment cannot result in the restoration of biomechanical stability of the knee joint or prevent the onset of conditions such as osteoarthritis.

Among the several objects and features of the present invention may be noted the provision of a method for repairing a tear in the meniscus which is less complex than existing methods; the provision of such a method which reduces trauma to the meniscus and knee joint; the provision of such a method which can be carried out from one side of the tear; and the provision of such a method which facilitates approximation of the tear so that the stability and resistance to disease of the knee joint is restored.

Further among the several objects and features of the present invention may be noted the provision of a system for carrying out the aforementioned method.

Other objects and features of the present invention will be in part apparent and in part pointed out hereinafter.

BRIEF DESCRIPTION OF THE DRAWINGS

FIGS. 2-5 are schematic views showing the use of the system to repair the torn meniscus;

FIG. 6 is a plan of the system showing the push rod pushing the tack along the delivering instrument; and FIG. 6A is a fragmentary longitudinal section of the instrument with the push rod and tack therein.

Corresponding reference characters indicate corresponding parts throughout the several views of the drawings.

DETAILED DESCRIPTION OF THE PREFERRED EMBODIMENT

Figure 1A:
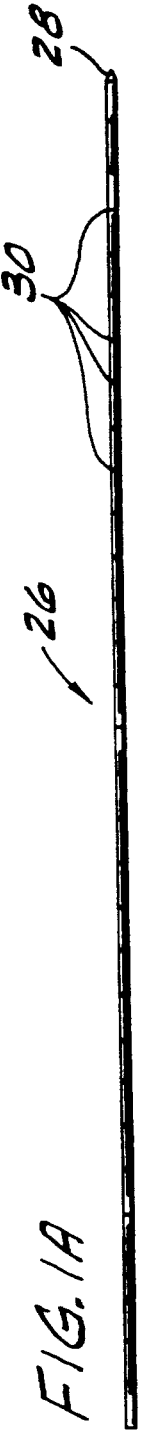
FIG. 1A is a plan of a guide pin of a system for repairing a tear to the meniscus.
Figure 1B:
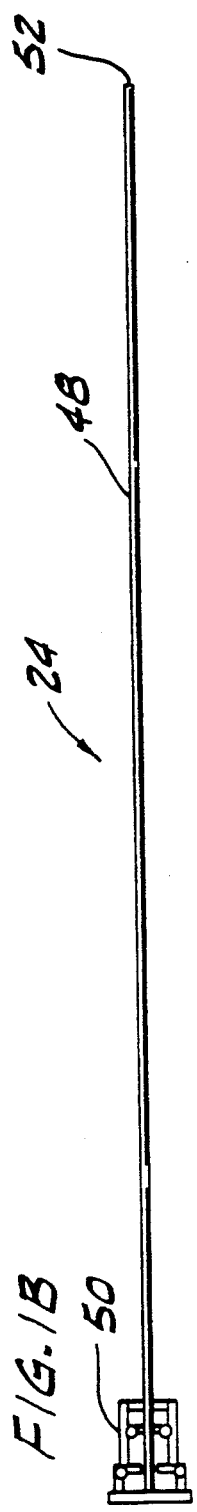
FIG. 1B is a plan of a push rod of the system.
Figure 1C:
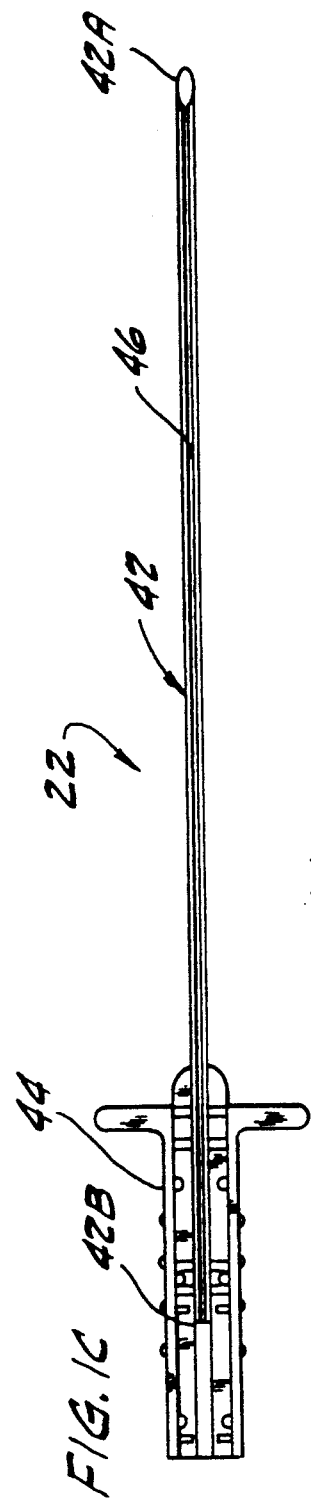
FIG. 1C is a plan of an instrument for delivering a suture to the tear in the meniscus.
Figure 1D:
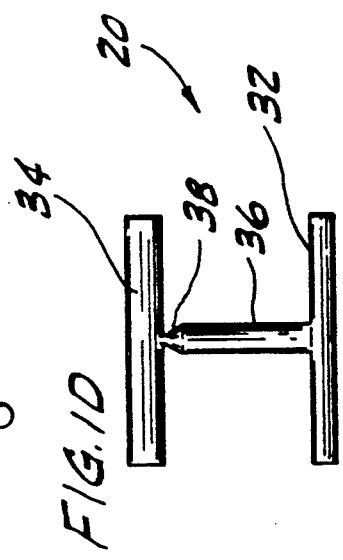
FIG. 1D is a greatly enlarged elevation of a suture tack of the system.

Referring now to the drawings a system for repairing a tear T in a meniscus M at a knee joint includes a tack (FIG. 1D, broadly "suture means") indicated generally at 20, an instrument for delivering the tack to the torn meniscus indicated generally at 22 (FIG. 1C), a push rod (FIG. 1B, broadly "pusher means") indicated generally at 24, and a guide pin indicated generally at 26 (FIG. 1A). The guide pin 26, which is preferably made of stainless steel, has a sharpened end 28 for piercing the meniscus M and a plurality of graduations 30 along its length for use in determining the appropriate size of tack 20 to use for closing the tear (FIG. 2). The use of the guide pin 26 and other components of the system will be described more fully below.

The tack 20 is generally H-shaped, having a first leg 32, a second leg 34 spaced from the first leg and a cross member indicated in its entirety by the reference numeral 36. The cross member 36 extends generally transversely with respect to the lengthwise extensions of the first and second legs 32, 34, and connects the first and second legs. The first and second legs 32, 34, and cross member 36 are generally cylindrical in shape with uniform diameters along their lengths, except the cross member has a tapered section 38 at its end connected to the second leg. The tack 20 is preferably made of an absorbable material of the type well known in the art, such as polyglycolic acid or polydioxane, which will be gradually absorbed by the body after it is used to suture the tear T. Thus, after approximation of the meniscus tissue, it is not necessary to surgically reenter the knee joint to remove the tack 20.

The delivery instrument 22 has an elongated shaft, generally indicated at 42, having a sharp first end 42A and a second end 42B opposite the first end which is mounted on a handle 44. The elongated shaft 42 has a longitudinally extending channel 46 which is generally circular in cross section and opens longitudinally outwardly at the first end 42A and the second end 42B of the shaft. As shown in FIG. 6A, the channel 46 is sized and shaped to receive the first leg 32 of the tack 20 with the cross member 36 and second leg 34 of the tack projecting out of the channel. The first leg 32 may slide longitudinally in the channel 46, but is held from substantial movement in directions transverse to the lengthwise extension of the channel.

The push rod 24 includes a slender rod 48 which is generally circular in cross section and sized and shaped for sliding reception in the channel 46 through the opening at the second end 42B of the elongated shaft 42. A handle 50 is attached to the rod 48 at one end to facilitate holding and manipulation of the rod. As shown in FIGS. 6 and 6A, an opposite end 52 of the rod 48 is constructed for engagement with the tack 20 in the channel 46 for pushing the tack in the channel from the second end 42B to the first end 42A of the elongated shaft 42, thereby to place the tack in the meniscus M for closing the tear T.

The procedure for repairing a tear T in the meniscus M typically begins by introducing saline solution into the knee through a large bore needle which pierces the knee through a small incision known as a portal to increase the working area around the knee joint. Equipment (not shown) continuously flushes the knee joint with saline solution, which is pumped into the knee and then withdrawn by the equipment. A cannula (not shown) is inserted through a second portal for carrying an arthroscope (not shown) into the knee so that the surgeon may observe the interior of the knee, including particularly the torn meniscus M. These steps are well known by those skilled in the art for preparation of the knee for arthroscopic surgery. It is to be understood that the precise preparatory steps may vary from the aforementioned and still fall within the scope of the present invention.

A third portal is made in the knee and another cannula (not shown) inserted through which the guide pin 26 is inserted to the vicinity of the tear T in the meniscus with the aid of the arthroscope. The sharpened end 28 of the guide pin is used to penetrate the meniscus M adjacent a first side F of the tear T in the meniscus. The guide pin 26 is pushed through the meniscus M and exits on a second side S of the tear T thereby forming a passage through the meniscus having an entrance on the first side F of the tear and an exit on the second side of the tear. The guide pin 26 is now positioned substantially as schematically shown in FIG. 2. The surgeon will either manipulate the guide pin 26 to close the tear or use another surgical tool (not shown), inserted through another portal in the knee, to close the tear. The surgeon then observes the guide pin 26 in the meniscus M using the arthroscope and determines the appropriate size of the tack 20 needed to close the tear T using the graduations 30 on the guide pin.

The guide pin 26 is now used to guide the delivery instrument 22 into position in the meniscus M. An unsharpened end 56 of the guide pin is received through the opening of the channel 46 in the first end 42A of the instrument 22 into the channel. The elongated shaft 42 is pushed down the guide pin 26 into the knee so that the first end 42A enters the passage formed in the meniscus M through its entrance on the first side F of the tear and leaves the passage through its exit on the second side S of the tear. The delivery instrument 22 is now generally in the position shown in FIG. 3 of the drawings. The guide pin 26 is withdrawn from the meniscus M and the knee through the opening in the channel 46 at the second end 42B of the elongated shaft, but the delivery instrument 22 stays in place substantially as shown in FIG. 4.

The surgeon has previously selected the appropriate size of tack 20 according to measurements made with the guide pin. The cross member 36 of the tack should be sufficiently short so that the first and second legs 32, 34, compress the meniscus enough to close the tear, but sufficiently long to allow the tack to be placed in the meniscus without damaging the meniscus tissue. Having selected the appropriately sized tack 20, the surgeon inserts the first leg 32 into the channel 46 through the opening at the second end 42B of the elongated shaft. The rod 48 of the push rod 24 is then telescopically received in the channel 46 through the opening at the second end 42B for pushing the first leg 32 of the tack down the channel thereby to deliver the tack to the tear T in the meniscus.

Upon reaching the first side F of the tear T in the meniscus M, the first leg 32 of the tack 20 passes through the entrance and into the passage in the meniscus (while remaining in the channel 46 of the delivery instrument 22). Initially, the second leg 34 and/or the cross member 36, which are disposed outside the channel 46, engage the meniscus M and are held from entering the passage. The obstruction provided by the meniscus M causes the cross member 36 and first leg 32 to resiliently flex relative to one another from their relaxed configuration to a configuration in which the cross member is nearly parallel to the lengthwise extension of the first leg. As the first leg 32 of the tack is pushed further through the passage toward its exit, the cross member 36 is drawn into the passage although it remains substantially outside the channel 46. The lengthwise extension of the second leg 34 is transverse to the lengthwise extension of the passage such that the second leg is adapted to engage the meniscus M around the entrance of the passage and will not enter the passage.

Eventually, the first leg 32 is pushed by the push rod 24 out of the passage and the channel 46 through the opening at the first end 42A of the elongated shaft 42, and the first leg moves back to its relaxed position relative to the cross member 36. In this position, the lengthwise extension of the first leg 32 is also transverse to the lengthwise extension of the passage so that the first leg is adapted to engage the meniscus M across the exit of the passage and cannot move back into the passage through the exit. The cross member 36 is disposed in the passage with its lengthwise extension parallel to that of the passage. The surgeon withdraws the delivery instrument 22 from the meniscus M and the knee, leaving the tack 20 in the position shown in FIG. 5. The first leg 32 and second leg engage and compress the meniscus M on the second side S and first side F of the tear T, respectively, to at least partially close the tear. If the tear T is sufficiently large a second tack 20' (shown in FIG. 6), having first and second legs 32' and 34', respectively, may have to be implanted in the meniscus M using substantially the same procedure as used for the first tack.

Once the appropriate number of tacks (e.g., tacks 20 and 20') have been placed in the meniscus M to properly close the tear T, the arthroscope is withdrawn and the portals made in the knee are sutured. The equipment (not shown) pumping saline solution into the knee joint is turned off and at least a portion of the saline is drained from the knee joint. The rest of the saline solution can be absorbed by the body. The patient is ready to begin recovery from the injury. As mentioned above, the tacks are made of material which is absorbable by the body so that, over time, they dissolve leaving only the repaired meniscus M.

In view of the above, it may be seen that the several objects and features of the present invention are achieved and other advantageous results attained in the method and system for repairing a tear T in the meniscus M described herein. A tack 20 may be implanted in the meniscus to close the tear T through a single passage in the meniscus M, thus lessening the trauma to the tissue. Moreover, there is no needle which must be passed back and forth through the meniscus M, out of and back into the knee thereby increasing the risk of accidental neurovascular damage to the knee. The system and method are simpler to use than existing systems and methods for repairing a torn meniscus M so that repair of the meniscus is a more viable treatment alternative to removal of the meniscus. Thus, with the system and method described herein the meniscus M is repaired and can again perform its vital functions of maintaining stability of the knee joint and preventing the onset of conditions such as osteoarthritis.

As various changes could be made in the above constructions without departing from the scope of the invention, it is intended that all matter contained in the above description or shown in the accompanying drawings shall be interpreted as illustrative and not in a limiting sense.

What is claimed is:

1. A method for repairing a tear in the meniscus at the knee joint, the method comprising the steps of:

making an incision generally at the knee for permitting access to the interior of the knee;

inserting an instrument through the incision to the vicinity of the tear in the meniscus;

entering the meniscus adjacent to a first side of the tear with an end of the instrument;

passing the end of the instrument through the meniscus and exiting the meniscus on a second side of the tear in the meniscus generally opposite the first side of the tear such that the instrument extends through a passage in the meniscus having an entrance on the first side of the tear and an exit on the second side of the tear;

delivering said suture means in the instrument to said passage, said suture means comprising a first leg, a second leg spaced from the first leg and a cross member extending generally transversely with respect to the lengthwise extension of the first and second legs and connecting the first and second legs;

pushing the first leg and cross member generally lengthwise into said passage through the entrance thereof with the first leg and the cross member being resiliently deflected from their relaxed positions relative to one another, the first leg moving back to its relaxed position relative to the cross member upon passing out of said passage through the exit thereof and leaving the instrument, the first leg thereafter extending transversely with respect to the lengthwise extension of said passage across the exit thereof and being adapted to engage the meniscus around the exit so that the first leg cannot move back into said passage through the exit, the second leg extending generally transversely with respect to the lengthwise extension of said passage across the entrance thereof and being adapted to engage the meniscus around the entrance of said passage so that the second leg cannot move into said passage through the entrance, and the cross member being disposed in said passage;

the cross member having a length less than the length of said passage such that the first leg and second leg compress the meniscus on opposite sides of the tear to at least partially close the tear.

2. A method as set forth in claim 1 wherein the instrument has an elongated channel therein opening at the end of the instrument which enters the meniscus and at an opposite end of the instrument located outside the knee, the channel being shaped and dimensioned for receiving the first leg of said suture means therein with the lengthwise extension of the first leg parallel to the lengthwise extension of the channel, and wherein the step of pushing the first leg and cross member comprises the steps of:

inserting the first leg of said suture means into the channel in the instrument with the leg being held from substantial radial movement in the channel;

inserting an end of a push rod into the channel from the end of the instrument outside the knee and engaging the first leg therewith;

sliding the push rod into the channel thereby pushing the first leg in the channel, through said passage in the meniscus and out of the channel at the end of the instrument which enters the meniscus; and withdrawing the instrument from the meniscus with said suture means remaining in the meniscus to close the tear therein.

3. A method as set forth in claim 2 further comprising, prior to the step of inserting the instrument through the incision, the steps of:

inserting elongated guide pin means through the incision to the vicinity of the tear in the meniscus;

penetrating the meniscus adjacent to a first side of the tear with an end of said guide pin means;

passing the end of said guide pin means through the meniscus and exiting the meniscus on a second side of the tear in the meniscus generally opposite the first side of the tear thereby to form said passage through the meniscus:

and wherein the steps of inserting the instrument through the incision, entering the meniscus and passing through said passage and exiting the meniscus comprise the steps of, sliding the instrument over said guide pin means at an end of said guide pin means opposite the end which penetrates the meniscus with said guide pin means being received in the channel of the instrument, pushing the instrument along said guide pin means toward the end of said guide pin means which penetrates the meniscus, the end of the instrument entering said passage in the meniscus through its entrance and exiting said passage through the exit, and wherein the method further comprises the step of withdrawing said guide pin means from the instrument and the knee through the opening in the channel at the end of the instrument outside the knee.

4. A method as set forth in claim 3 wherein the method further comprises the step, prior to said step of withdrawing said guide pin means from the instrument, of gauging the proper size of suture means needed to close the tear using longitudinally spaced graduations on said guide pin means.

5. A method as set forth in claim 2, and wherein the method further comprises, prior to the step of inserting the instrument through the incision, the steps of:

inserting elongated guide pin means through the incision to the vicinity of the tear in the meniscus said guide pin means having longitudinally spaced graduations thereon;

penetrating the meniscus adjacent to a first side of the tear with an end of said guide pin means;

passing the end of said guide pin means through the meniscus and exiting the meniscus on a second side of the tear in the meniscus generally opposite the first side of the tear thereby to from said passage through the meniscus;

closing the tear;

gauging the size of suture means needed to close the tear using the graduations on said guide pin.

6. A system for repairing a tear in the meniscus in the knee joint, the system comprising:

suture means having a first leg, a second leg spaced from the first leg and a cross member extending generally transversely with respect to the lengthwise extensions of the first and second legs and connecting the first and second legs;

an instrument for delivering said suture means to the meniscus, the instrument being adapted for insertion through an incision in the knee and into the vicinity of the meniscus, a first end of the instrument being adapted to enter the meniscus adjacent to a first side of the tear, passing through the meniscus and exiting the meniscus on a second side of the tear in the meniscus generally opposite the first side of the tear such that the instrument extends through a passage in the meniscus having an entrance on the first side of the tear and an exit on the second side of the tear;

the instrument having a channel therein extending longitudinally of the instrument and opening at the first end, the first leg of said suture means being adapted for insertion into the channel and for sliding movement generally longitudinally of the channel, the channel being dimensioned and shaped so that the first leg is held from substantial movement in the channel in directions transverse to the lengthwise extension of the channel;

pusher means for pushing the first leg and cross member of said suture means generally lengthwise in the channel and into said passage through the entrance thereof with the first leg and the cross member being resiliently deflected from their relaxed positions relative to one another, the first leg moving back to its relaxed position relative to the cross member upon leaving said passage through the exit thereof, the first leg thereafter extending transversely with respect to the lengthwise extension of said passage across the exit thereof and being adapted to engage the meniscus around the exit so that the first leg cannot move back into said passage through the exit, the second leg being adapted to extend generally transversely with respect to the lengthwise extension of said passage across the entrance thereof and to engage the meniscus around the entrance of said passage so that the second leg cannot move into said passage through the entrance, and the cross member being disposed in said passage;

the cross member having a predetermined length such that the first leg and second leg compress the meniscus on opposite sides of the tear to at least partially close the tear;

elongated guide pin means having a plurality of longitudinally spaced graduations thereon and a sharpened end for penetrating the meniscus adjacent to the first side of the tear, the sharpened end being adapted to pass through the meniscus and exit the meniscus on the second side of the tear in the meniscus generally opposite the first side of the tear thereby to from said passage through the meniscus, said guide pin means being sized and shaped to be received in the channel of the instrument for guiding insertion of the instrument into and through said passage in the meniscus.

7. A system as set forth in claim 6 wherein said suture means is generally H-shaped.

8. A system as set forth in claim 7 wherein said suture means is made of material which is capable of being absorbed by the body.

9. A system as set forth in claim 6 wherein said guide pin means has a plurality of longitudinally spaced graduations thereon for use in gauging the size of the tear in the meniscus for use in determining the proper size of said suture means needed to close the tear.

10. A system as set forth in claim 6 wherein said pusher means comprises an elongated pusher rod sized and shaped for reception in the channel and for sliding longitudinally in the channel, an end of the pusher rod being adapted to engage the first leg in the channel of the instrument for pushing the first leg in the channel.

11. A system as set forth in claim 10 wherein said pusher rod has a handle mounted generally on its ends opposite the end adapted to engage the first leg of said suture means in the channel.

12. A system for repairing a tear in the meniscus in the knee joint, the system comprising:

suture means having a first leg, a second leg spaced from the first leg and a cross member extending generally transversely with respect to the lengthwise extensions of the first and second legs and connecting the first and second legs;

an instrument for delivering said suture means to the meniscus, the instrument being adapted for insertion through an incision in the knee and into the vicinity of the meniscus, a first end of the instrument being adapted to enter the meniscus adjacent to a first side of the tear, passing through the meniscus and exiting the meniscus on a second side of the tear in the meniscus generally opposite the first side of the tear such that the instrument extends through a passage in the meniscus having an entrance on the first side of the tear and an exit on the second side of the tear;

the instrument having a channel therein extending longitudinally of the instrument and opening at the first end and at a second end of the instrument opposite the first end, the first leg of said suture means being adapted for insertion into the channel generally at the second end thereof and for sliding movement generally longitudinally of the channel, the channel being dimensioned and shaped so that the first leg is held from substantial movement in the channel in directions transverse to the lengthwise extension of the channel;

said suture means being movable generally lengthwise in the channel and into said passage through the entrance thereof with the first leg and the cross member being resiliently deflected from their relaxed positions relative to one another, the first leg moving back to its relaxed position relative to the cross member upon passing out of said passage through the exit thereof and leaving the instrument, the first leg thereafter extending transversely with respect to the lengthwise extension of said passage across the exit thereof and being adapted to engage the meniscus around the exit so that the first leg cannot move back into said passage through the exit, the second leg extending generally transversely with respect to the lengthwise extension of said passage across the entrance thereof and being adapted to engage the meniscus around the entrance of said passage so that the second leg cannot move into said passage through the entrance, and the cross member being disposed in said passage;

the cross member of said suture means having a predetermined length such that the first leg and second leg compress the meniscus on opposite sides of the tear to at least partially close the tear;

elongated guide pin means having a plurality of longitudinally spaced graduations thereon and a sharpened end for penetrating the meniscus adjacent to the first side of the tear, the sharpened end being adapted to pass through the meniscus and exit the meniscus on the second side of the tear in the meniscus generally opposite the first side of the tear thereby to form said passage through the meniscus, said guide pin means being sized and shaped to be received in the channel of the instrument for guiding insertion of the instrument into and through said passage in the meniscus.

13. A system as set forth in claim 12 wherein said guide pin means has a plurality of longitudinally spaced graduations thereon for use in gauging the size of the tear in the meniscus for use in determining the proper size of said suture means needed to close the tear.

14. A system as set forth in claim 12 wherein said suture means is generally H-shaped.

15. A system as set forth in claim 14 wherein said suture means is made of material which is capable of being absorbed by the body.

16. A system as set forth in claim 12 further comprising an elongated pusher rod sized and shaped for reception in the channel and for sliding longitudinally in the channel, an end of the pusher rod being adapted to engage the first leg in the channel of the instrument for pushing the first leg in the channel.

17. A system as set forth in claim 16 wherein said pusher rod has a handle mounted generally on its end opposite the end adapted to engage the first leg of said suture means in the channel.

* * * * *